United States Patent
Ehehalt et al.

(10) Patent No.: US 8,322,202 B2
(45) Date of Patent: Dec. 4, 2012

(54) METHOD FOR INSPECTING A TURBINE INSTALLATION AND CORRESPONDING DEVICE

(75) Inventors: Ulrich Ehehalt, Essen (DE); Scarlett Fajardo-Reina, Ratingen (DE); Daniel Grundei, Oberhausen (DE); Harald Harders, Mülheim a.d. Ruhr (DE); Stefan Krause, Krefeld (DE); Martin Krompietz, Essen (DE); Andreas Lüttenberg, Essen (DE); Christoph Pels Leusden, Nürnberg (DE); Wilhelm Scheidtmann, Iserlohn (DE); Eckart Schumann, Mülheim an der Ruhr (DE); Thomas-Dieter Tenrahm, Dinslaken (DE); Dirk Trenaman, Oviedo, FL (US)

(73) Assignee: Siemens Aktiengesellschaft, München (DE)

( * ) Notice: Subject to any disclaimer, the term of this patent is extended or adjusted under 35 U.S.C. 154(b) by 810 days.

(21) Appl. No.: 12/225,252

(22) PCT Filed: Jan. 26, 2007

(86) PCT No.: PCT/EP2007/050767
§ 371 (c)(1),
(2), (4) Date: Jul. 16, 2009

(87) PCT Pub. No.: WO2007/107395
PCT Pub. Date: Sep. 27, 2007

(65) Prior Publication Data
US 2009/0293596 A1 Dec. 3, 2009

(30) Foreign Application Priority Data

Mar. 17, 2006 (EP) .................................... 06005567

(51) Int. Cl.
*G01M 15/14* (2006.01)
(52) U.S. Cl. .................................................. 73/112.01
(58) Field of Classification Search ............... 73/112.01, 73/112.02, 112.03, 118.03
See application file for complete search history.

(56) References Cited

U.S. PATENT DOCUMENTS 3,731,070 A    5/1973 Urban
5,125,035 A *  6/1992 McCarthy et al. ............ 382/141
(Continued)

FOREIGN PATENT DOCUMENTS

DE    198 43 615 A1    4/2000
(Continued)

OTHER PUBLICATIONS

Amory, D.C. et al; "Improving Gas Turbine Efficiency Using Optical Pyrometry"; Turbomachinery Internation, Business Journals, Jan. 2004; pp. 22-24; vol. 45, No. 1; XP001190994; ISSN: 0149-4147; Norvalk, CT, USA.

*Primary Examiner* — Eric S McCall

(57) ABSTRACT

The invention relates to a method for inspecting especially a gas turbine installation or steam turbine installation. An actual condition of a component of the turbine installation is determined using a suitable system, the determined actual condition is compared with a predetermined desired condition of the component, and the result of comparison between the actual condition and the desired condition is used to determine whether an overall inspection of the turbine installation is required. The component is a guide vane whose angular position in relation to the direction of influx is the actual condition to be determined. The actual condition is determined by an imaging device. The invention also relates to a turbine inspection system for carrying out the method.

1 Claim, 1 Drawing Sheet

U.S. PATENT DOCUMENTS

| | | |
|---|---|---|
| 5,938,401 A | 8/1999 | Modeen et al. |
| 6,109,783 A | 8/2000 | Dobler et al. |
| 6,364,524 B1 | 4/2002 | Markham |
| 6,992,315 B2 * | 1/2006 | Twerdochlib ............ 250/559.08 |
| 7,116,839 B2 * | 10/2006 | Leboeuf ........................ 382/286 |
| 7,502,538 B2 * | 3/2009 | Brummel et al. ............. 385/120 |
| 2004/0079070 A1 | 4/2004 | Macchia |
| 2005/0199832 A1 * | 9/2005 | Twerdochlib ............ 250/559.29 |
| 2007/0157733 A1 * | 7/2007 | Litzenberg et al. ............ 73/644 |
| 2008/0310804 A1 * | 12/2008 | Brummel et al. ............. 385/115 |
| 2011/0211940 A1 * | 9/2011 | George et al. ..................... 415/1 |

FOREIGN PATENT DOCUMENTS

| | | |
|---|---|---|
| EP | 1 227 222 A2 | 7/2002 |
| EP | 1 314 872 A1 | 5/2003 |
| EP | 1 408 201 A2 | 4/2004 |
| EP | 1 482 275 A1 | 12/2004 |

* cited by examiner

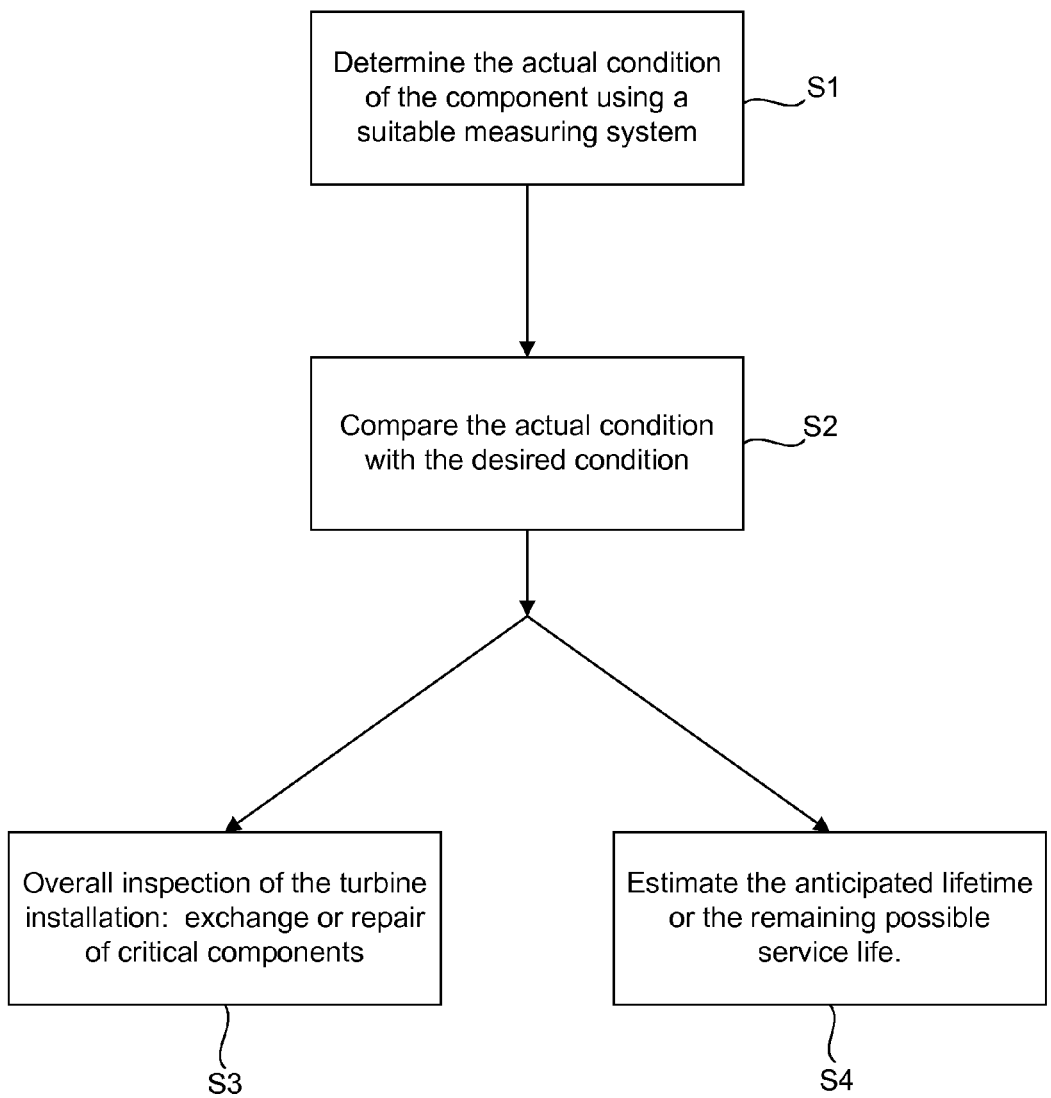

METHOD FOR INSPECTING A TURBINE INSTALLATION AND CORRESPONDING DEVICE

CROSS REFERENCE TO RELATED APPLICATIONS

This application is the US National Stage of International Application No. PCT/EP2007/050767, filed Jan. 26, 2007 and claims the benefit thereof. The International Application claims the benefits of European application No. 06005567.0 filed Mar. 17, 2006, both of the applications are incorporated by reference herein in their entirety.

FIELD OF INVENTION

The invention relates to a method for inspecting power conversion machines, in particular a gas turbine installation or a steam turbine installation. The invention furthermore relates to an inspection system for a turbine installation to carry out the method according to the invention.

BACKGROUND OF THE INVENTION

Currently, turbine installations are subject to an overall inspection during which the entire turbine installation is generally shutdown in the basis of an empirical variable applicable to the entire turbine. During these downtimes, critical components of the turbine installation, such as the guide vanes and rotor blades or combustion chamber linings, for example, are inspected in more detail to determine whether the condition of the components permits further use of these components in the operation of the turbine installations or whether replacement or overhaul of the components may be necessary in order to prevent failure during the operation of the turbine installation.

By way of example, the effective operating hours (abbreviated EOH) can be the significant variable which governs the maintenance downtimes and is calculated using empirical formulae. The following input variables are conceivable: the operating hours (abbreviated OH) of the turbine installation, the so-called dynamic hours (abbreviated Dyn H), that is to say the operating hours during which the turbine installation is subject to large changes in the operating state (which are linked to large changes in the load, particularly thermal load changes on the components of the turbine installation), and the number of turbine initializations, are included.

It is conventional to carry out an inspection of a turbine installation after the course of a predetermined number of effective operating hours.

However, the influence of the actual load, the set turbine inlet temperature and the fuel are ignored in this known inspection method. Furthermore, a particular, component-specific finding progress, in the form of crack growth for example, is also not considered. The components of the turbine installation are usually only examined and no measures for possible repairs are derived on the basis of the undertaken inspection. The only components that can be and are also replaced within the course of inspections are ceramic and metallic heat shields, with the ceramic heat shields being replaced, if applicable, by means of an empirically set crack length criterion based on visual inspection, and, in this case, the life of the heat shields is not usually utilized to its full extent.

When taking everything into consideration, it should therefore firstly be noted that known inspection methods often do not utilize the life of the components of turbine installations optimally. Furthermore, the components are only examined during the downtimes provided for the overall inspection, so that possibly critically damaged components may not be identified at an early enough stage, which is linked to a risk during the operation of the turbine installation which cannot be ignored.

Furthermore, EP 1 227 222 A2 discloses a method for determining the time for servicing a gas turbine. The time for servicing is determined in this case as a function of the wear of a monitored turbine blade, with the wear of the turbine blade being determined by means of a temperature sensor.

Furthermore, DE 198 43 615 A1 discloses a servicing monitoring unit for calculating and displaying the due date of the next servicing of a combustion drive. The servicing monitoring unit in this case observes the temporal profiles of the actual values of operating signals or parts thereof (for example, the rotor rotational speed) and derives conclusions about an inspection being required soon.

SUMMARY OF INVENTION

The invention is based on the object of specifying a method for inspecting a turbine installation, by means of which the life, in particular of critical components of the turbine installation, can be utilized to its full extent in an optimal manner and without risk.

According to the invention, this object is achieved by a method according to the claims.

By using suitable means, preferably in the form of technical instruments, provided for determining the actual conditions of in particular critical components of the turbine installation, the actual condition of the components can be determined even while the turbine is operating. In this context, the actual condition of a component is preferably understood to mean every technical feature of a component which influences the serviceability and life of the component.

The determined actual condition of the respective component can then be compared with a predetermined desired condition at any given time while the turbine is operating. Based on this comparison according to the invention between the actual condition and a predetermined desired condition which corresponds to a serviceable state of the relevant component of the turbine installation, according to the invention it is then possible to derive whether an overall inspection of the turbine installation, during which the turbine installation is generally shutdown, is necessary.

Within the scope of the overall inspection, it is then possible to once again examine in depth the components concerned and further critical components as to whether they are serviceable. In this case, it may possibly be necessary to replace corresponding components or undertake suitable repairs.

According to the invention, the at least one component of the turbine installation comprises the guide vanes of the compressor which can be adjusted relative to the outlet flow, with the actual condition to be determined being the angular position of the guide vanes relative to the inlet flow direction, and the means is an imaging device, in particular a camera, with image records of the guide vane being taken by the imaging device to determine the angular position in order to make the decision relating to the overall inspection dependent on this condition.

It is possible that the variable angular position of guide vanes, in particular of variable guide vanes in compressors, can be varied by mechanical or thermal loads which can have negative consequences for the efficiency of the turbine. By means of the method according to the invention, it is possible that the actual condition, characterized by the angular position of the guide vanes relative to the inlet flow direction, can be determined by using an imaging device, in particular a camera, and can be directly compared with appropriate requirements for uniform angular positions which cover the desired condition.

If the deviations of the angular adjustment between actual condition and desired condition become too large, or in case different angular settings of individual guide vanes of the guide vane assembly occur along the circumference of the annular channel of the compressor, an overall inspection may be necessary.

When taking everything into consideration, the method according to the invention allows risk-free optimal utilization of the lives of critical components of a turbine installation. This can increase the availability of the turbine installation. This holds in particular for turbine installations which are operated carefully and which, according to the abovementioned empirical formulae known from the prior art for calculating effective operating hours, would be subject to an overall inspection more often than technically necessary. According to the invention, it is thus possible to save a number of downtime-days per year.

In one advantageous development of the method according to the invention, a further component of the turbine installation additionally monitored during the operation is a filter, the actual condition to be determined being the state of contamination of the filter, and a pressure measurement apparatus is used as the associated means, in which the pressure drop across the filter, which occurs when flow passes through the filter, is measured by the pressure measurement apparatus to determine the state of contamination of the filter.

In one specific application, the filter is preferably an intake filter in an intake housing of the compressor of a turbine installation. The state of contamination is directly linked in a known manner to the pressure drop across the filter and thus, according to the invention, it can be quantified whilst the turbine is operating. The pressure drop is measured by means of a conventional pressure measurement apparatus. In this practical development of the method according to the invention, the actual condition determined in this manner is compared with the desired condition, which is in the form of a predetermined value or value range for the pressure drop. If a deviation from the desired condition which can no longer be tolerated is determined, the turbine installation should be shutdown to carry out an overall inspection in which the intake filter should be removed from the intake housing and be replaced by a new or repaired intake filter.

Furthermore, the state of contamination or erosion of the blades can also be inferred from the state of contamination of an external filter in the cooling circuit of a turbine installation, which state is determined by a pressure drop measurement.

In one advantageous embodiment, an additionally monitored component of the turbine installation is a blade, the actual condition to be determined is the material characteristics of the blade, and a thermographic measurement apparatus is used as the associated means, with a thermographic measurement of the blade being undertaken to determine the material characteristics and the measurement being carried out using the thermographic measurement apparatus.

By means of a thermographic measurement of the guide vanes and/or rotor blades in the first turbine stage, the actual condition of the blades in terms of their material characteristics can be determined. By means of a thermographic measurement, lamination, cracks and scaling on the blades can be recognized. In this case, the desired condition comprises for example a correspondingly usable blade, the lamination and scaling of which still ensuring reliable use of the blade over sufficient operating hours. In particular, the desired condition can comprise information relating to the shape, in particular the length, of still uncritical cracks which can be compared with measured cracks to evaluate the actual condition.

If the deviations from the desired condition predetermined in this way are too large, or no longer tolerable, the turbine installation should be shutdown to carry out an overall inspection, in which the blades and, if applicable, further components must be replaced or overhauled.

In a further practical development of the method according to the invention, a structure-borne sound measurement apparatus can be used as associated means for determining the material characteristics instead of the thermographic measurement apparatus, by means of which the abovementioned features of material fatigue of the blades, in particular cracks, can be determined their size and means can be quantified a structure-borne sound measurement.

In further developments of the method according to the invention, it is additionally possible to determine the material characteristics or integrity of combustion chamber linings and heat shields, in particular ceramic heat shields and metallic heat shields, using structure-borne sound measurement apparatuses and thermographic measurement apparatuses, and to compare them with corresponding desired conditions to determine the material characteristics, as explained above. According to the invention, the measurement results achieved with both the structure-borne sound measurement apparatus and the thermographic measurement apparatus can be coordinated or combined to determine the respective actual conditions of the above components with the greatest possible precision and to permit a meaningful evaluation of the actual conditions by subsequent comparison with the corresponding desired conditions which may make an overall inspection of the turbine installation necessary.

The invention further relates to an inspection system for a turbine installation for carrying out the method according to the invention with at least one means provided to determine the actual condition of at least one selected component of the turbine installation, and at least one evaluation unit designed to receive and evaluate the actual condition determined by the at least one means and compare it with at least one predetermined desired condition, in which, in one preferred embodiment, the evaluation unit is furthermore designed to determine whether an overall inspection of the turbine is necessary, by comparing the determined actual condition with the desired condition.

Preferably, a number of different components are monitored simultaneously; in this case it is possible for different desired conditions of the individual components to be predetermined if applicable. If wear occurs in two or more components, an overall inspection which is carried out earlier can be expedient compared with an overall inspection which is carried out later and is initiated by only one component considered on its own.

BRIEF DESCRIPTION OF THE DRAWINGS

The FIGURE illustrates a flow chart depicting a method for inspecting a gas or steam turbine installation, in accordance with the present invention.

DETAILED DESCRIPTION OF INVENTION

As is shown in the FIGURE, using the method according to the invention, the actual condition of the respective component of the turbine installation is firstly determined by means of a suitable measuring device (cf. step S1). Subsequently, the determined actual condition is compared with a predetermined desired condition (cf. step S2). In the next step (cf. step S3), a decision is made on the basis of the comparison as to whether an overall inspection of the turbine installation is necessary, in which case the turbine installation is shutdown and appropriate components are replaced or repaired. If this is not the case (cf. step S4), the anticipated life is estimated, for example by means of a crack propagation model or an estimate of the operating hours possible.

The invention claimed is:

1. A method for inspecting a gas or steam turbine installation, comprising:
   determining an actual condition of a component of the turbine installation via an associated device;
   comparing the determined actual condition in each case with a predetermined desired condition of the respective component; and
   using the comparison of the actual condition with the respective desired condition to determine whether an overall inspection of the turbine installation is necessary,
   wherein the component is a guide vane having an angular position relative to an inlet flow direction,
   wherein the associated device is a camera,
   wherein the actual condition to be determined is the angular position of the guide vane relative to the inlet flow direction, and
   wherein an image record of the guide vane are taken by the camera to determine the angular position.

* * * * *